United States Patent [19]

Brown

[11] 4,109,692
[45] Aug. 29, 1978

[54] ENCAPSULATING DEVICE FOR GAS CYLINDER

[76] Inventor: Roland H. Brown, 13409 Conch Ct., Tampa, Fla. 33618

[21] Appl. No.: 811,487

[22] Filed: Jun. 30, 1977

[51] Int. Cl.² .......................................... B65D 61/00
[52] U.S. Cl. ................................ 150/52 R; 215/12 R; 220/85 P
[58] Field of Search ............... 150/52 R, 52 H, 52 G; 220/85 P; 215/12 R; 24/230 BC

[56] References Cited

U.S. PATENT DOCUMENTS

| | | |
|---|---|---|
| 815,971 | 3/1906 | Mulnaney et al. ............... 215/12 R |
| 1,013,693 | 1/1912 | Steel ................................. 215/12 R |
| 1,132,180 | 3/1915 | Hales ................................ 215/12 R |
| 1,941,258 | 12/1933 | Gordon ........................... 24/230 BC |
| 2,256,521 | 9/1941 | Kirkpatrick ...................... 150/52 G |
| 2,465,095 | 3/1949 | Harvey ............................. 220/85 P |
| 2,838,085 | 6/1958 | Beeler .............................. 150/52 R |
| 3,061,135 | 10/1962 | Martin ............................. 215/12 R |
| 3,691,294 | 9/1972 | Charles ............................ 150/52 R |
| 4,022,343 | 5/1977 | Richardson ...................... 150/52 R |

Primary Examiner—Herbert F. Ross
Attorney, Agent, or Firm—Arthur W. Fisher, III

[57] ABSTRACT

An encapsulating device for gas cylinders having a valve and gauge assembly thereon. The encapsulating device comprises a cage assembly for the enclosure and protection of the gas cylinder having a valve and gauge assembly, and an enclosure bag disposed around the outside of the cage assembly. The cage assembly comprises a base to support the cage assembly, a protective ring of a size to surround the valve and gauge assembly, and at least one pair of legs fixedly attached at one end to the base and the opposite end to the protective ring. The length of the legs is such that the protective ring is disposed in surrounding and protecting relation with the valve and gauge assembly. The encapsulating device further comprises a first and a second retainer to retain the gas cylinder within the cage assembly.

6 Claims, 6 Drawing Figures

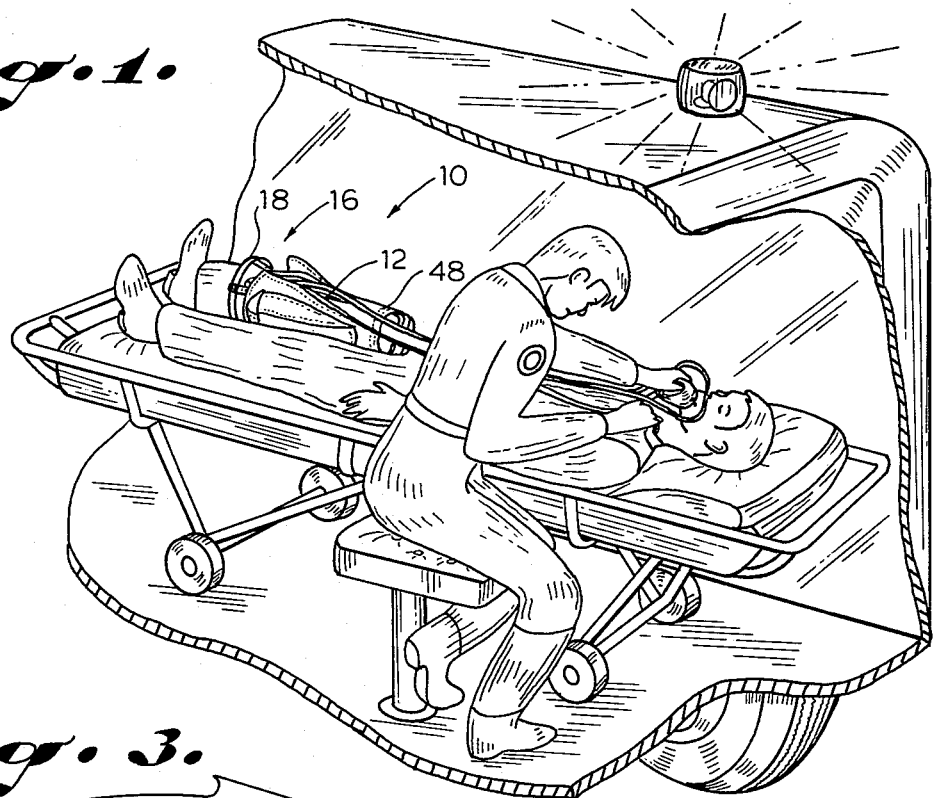
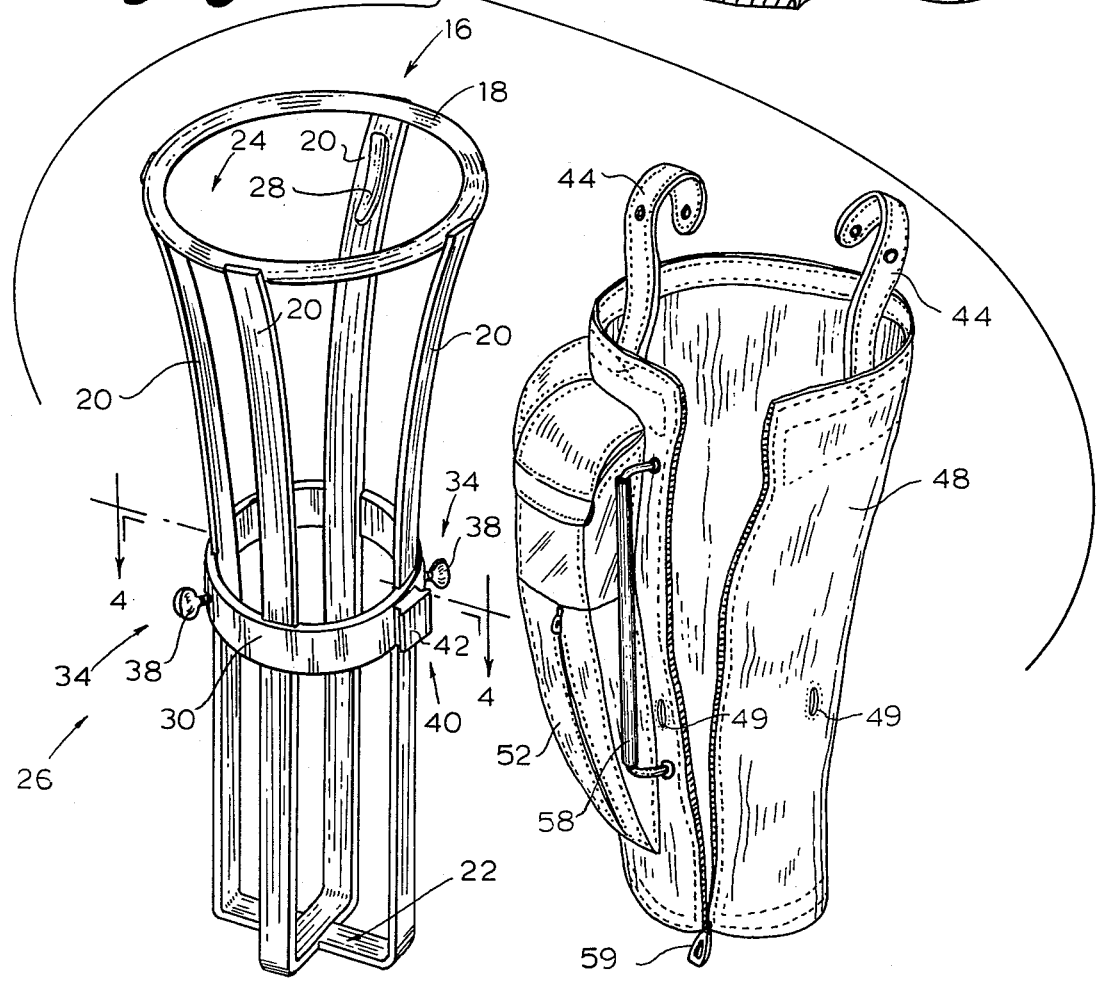

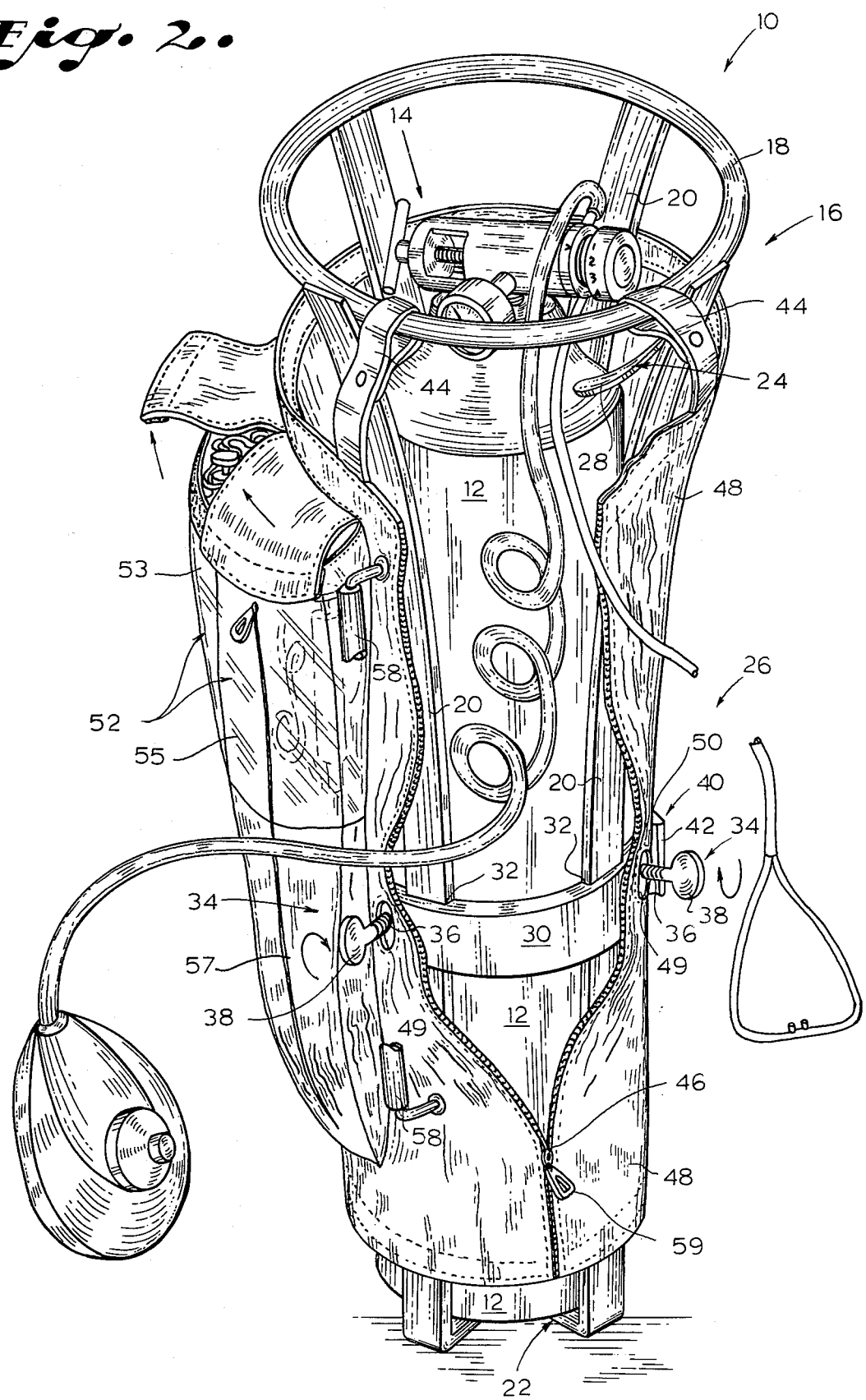

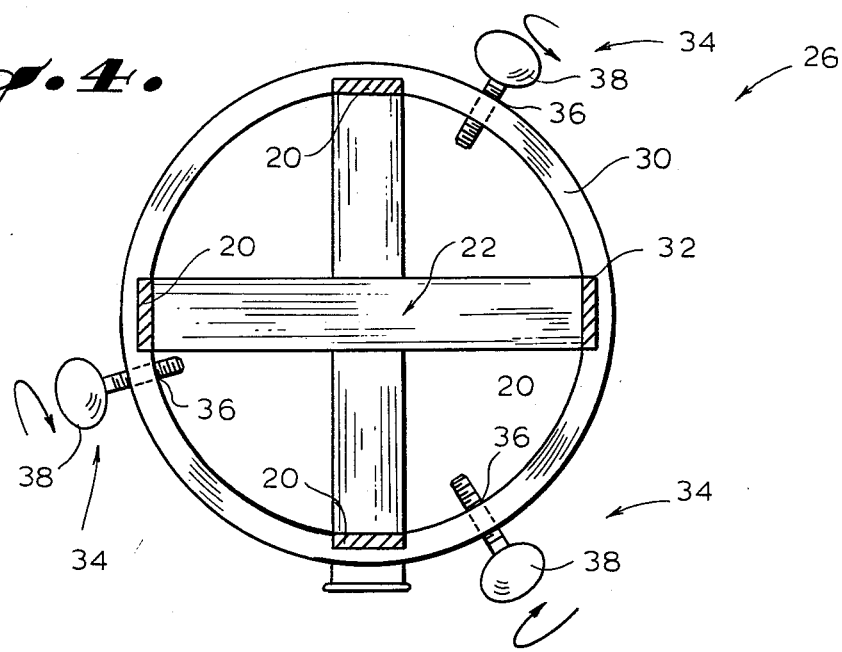
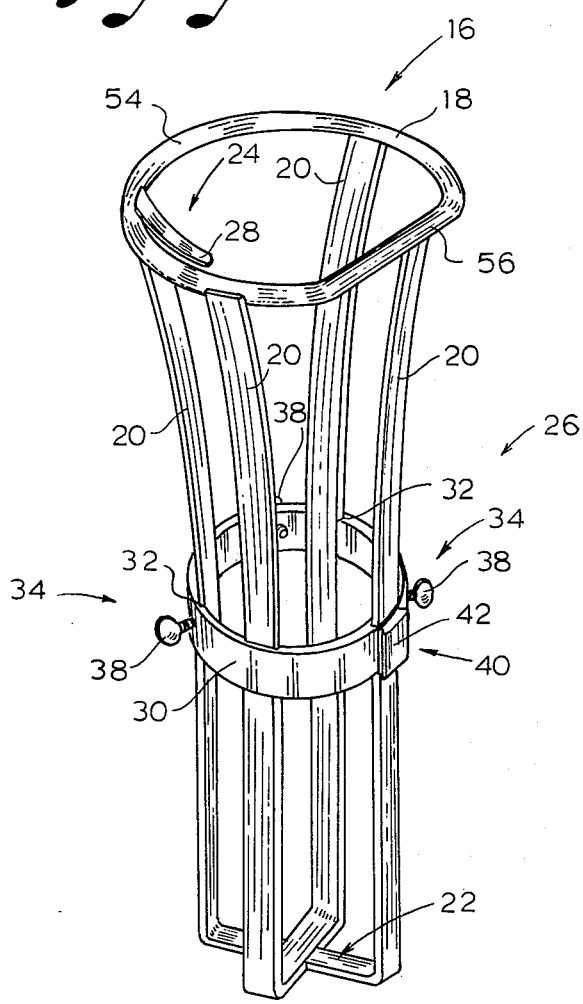
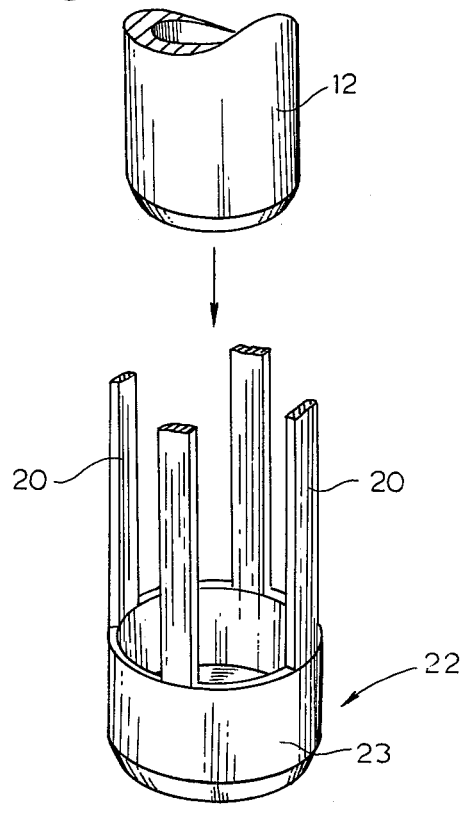

ENCAPSULATING DEVICE FOR GAS CYLINDER

BACKGROUND OF THE INVENTION

1. Field of the Invention

An encapsulating device for gas cylinders having a valve and gauge assembly thereon.

2. Description of the Prior Art

In the field of emergency medical services, portable oxygen cylinders presently are enclosed by heavy and cumbersome boxes as standard equipment. Usually, the cylinder is placed on the stretcher with the patient between his legs. This necessarily requires that the cylinder be removed from its bulky enclosure.

Gas cylinders contain valve and gauge assemblies thereon which are subject to being damaged in the gas cylinders are dropped or tipped over moreover potential injuries to individuals nearby are significant.

The prior art includes a protective ring disposed in surrounding and protecting relation with the valve and gauge assembly. The protective ring is fixedly attached to the cylinder by means of a pair of brackets and arms.

Examples of the prior art are shown in U.S. Pat. Nos. 3,503,536; 3,576,341; 3,756,450; 3,776,412; 3,831,802; and 3,848,768. With the exception of U.S. Pat. No. 3,576,341, each shows a simple cap or ring for enclosing the valve portion of the gas cylinder without means of encapsulating and stabilizing the entire device or means to facilate use of auxiliary equipment. U.S. Pat. No. 3,576,341 shows a simple stand without protective means.

What is needed is a self-contained encapsulating device which is light and includes a protective ring disposed in surrounding and protecting relation with the valve and gauge assembly. Such a device can be used with existing gas cylinders as well as ones to be produced, and will protect the valve and gauge assembly from damage in case the gas cylinder is dropped or tipped over.

SUMMARY OF THE INVENTION

This invention relates to a portable gas cylinder encapsulating device for the enclosure and protection of portable gas cylinders and especially the protection of the valve and gauge assemblies thereon. The encapsulating device comprises a cage assembly and an enclosure bag removably attached to and disposed to substantially surround the cage assembly.

The cage assembly comprises a protective ring, at least one pair of legs fixedly attached thereto, and a base fixedly attached between the legs. The central axis of the gas cylinder is disposed to run substantially through the center of the protective ring which is substantially larger than that of the gas cylinder and such that it substantially encloses the valve and gauge assembly at any point along the axis of the gas cylinder The length of the legs is such that the protective ring is fixedly disposed in annularly surrounding and protecting relation with the valve and gauge assembly.

The cage assembly further comprises a first and a second retainer means to retain the gas cylinder within the encapsulating device when tipped over. The first retainer means comprises a spring member fixedly attached to the upper portion of a leg and disposed in a first position such that its lower portion is disposed above the upper portion of the gas cylinder to engage the upper portion for retention thereof within the encapsulating device. The spring member is movable to a second position wherein the lower portion of the spring member substantially engages the leg so that the gas cylinder can be removed from the encapsulating device. The second retainer means comprises a retainer ring disposed to surround and engage the gas cylinder at or near the central portion thereof and a holding means to fixedly engage the gas cylinder.

The encapsulating device further includes an attachment means fixedly attached to the retainer ring for the removable attachment of the encapsulating device with gas cylinder to the wall of a structure for storage there and for quick removal for emergency use.

In operation, the protective ring acts as a convenient handle and the gas cylinder is easily placed between a patient's legs while on a stretcher without the necessity of removal from the encapsulating device. Because of the light weight of the encapsulating device, there is little temptation to remove the gas cylinder therefrom.

In case of accidental dropping of the gas cylinder, it is retained securely within the encapsulating device by the first and second retainer means and the valve and gauge assembly is protected from damage by the protective ring. Moreover the neck of the gas cylinder is similarly protected, thereby preventing damage thereto which might otherwise cause the extremely high pressure gas cylinder to become a projectile.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which:

FIG. 1 is a perspective view of the preferred embodiment as it would be viewed while in use.

FIG. 2 is a perspective view of the perferred embodiment with portions removed outward from their original positions inside.

FIG. 3 is an exploded perspective view of the cage assembly and enclosure bag.

FIG. 4 is a sectional view at a line drawn at 4—4 on FIG. 3.

FIG. 5 is a perspective view showing an alternate embodiment of alternate protective ring.

FIG. 6 is a perspective view showing an alternate embodiment of an alternate base comprised of a cup arrangement.

Similar reference characters refer to similar parts throughout the several views of the drawings

DETAILED DESCRIPTION OF THE PREFERRED EMBODIMENT

As best shown in FIGS. 1 and 2, this invention relates to a portable gas cylinder encapsulating device generally indicated as 10 for the enclosure and protection of portable gas cylinders 12 and especially the protection of the valve and gauge assembly 14 thereon. The encapsulating device 10 comprises a cage assembly 16 and an enclosure bag removably attached to and disposed to substantially surround the cage assembly 16.

As best shown in FIG. 2, the cage assembly 16 is made from steel or other suitable material to provide rigidity and strength. The cage assembly 16 comprises a substantially annular protective ring 18, at least one pair of legs 20 fixedly attached to the protective ring 18, and a base 22 fixedly attached to the lower portions of the legs 20 and disposed below the lower portion of the gas cylinder 12 for support thereof. Each leg 20 is a strip or bar of sufficient size to provide the necessary rigidity and strength but yet small enough to maintain an overall light weight. The base 22 comprises other strips or bars fixedly attached between each pair of legs 20. Each pair of legs 20 and its respective base strip may comprise a single strip of metal bent at substantially 90 degree angles to form each leg 20. Alternately the base 22 may comprise a cup like element 23 to receive the lower portion of the gas cylinder 12. The diameter of the base 22 is substantially equal to the diameter of the gas cylinder 12 while the diameter of the protective ring 18 is substantially twice the diameter of the gas cylinder 12. It is of importance that the resulting contour of the cage assembly 16 follows the natural contour of the subject's legs in the prone position. Thus use does not interfere with body's natural posture.

The central axis of the gas cylinder 12 is disposed to run substantially through the center of the protective ring 18. The diameter of the protective ring 18 is substantially larger than the diameter of the gas cylinder 12 and such that it substantially encloses the valve and gauge assembly 14.

The length of the legs 20 is such that the protective ring 18 is fixedly disposed in annularly surrounding and protecting relation with the valve and gauge assembly 14. Specifically, the protective ring 18 is fixedly disposed above the top portion of the valve and gauge assembly 14 or around the top portion thereof.

The cage assembly 16 further comprises a first and a second retainer means 24 and 26 respectively to retain the gas cylinder 12 within the encapsulating device 10 when tipped over.

As shown in FIG. 3 the first retainer means 24 comprises at least one spring member 28 fixedly attached to the upper portion of a leg 20. The spring member 28 comprises at strip of flexible metal or other material rigidly disposed in a first position such that its lower portion is disposed above the upper portion of the gas cylinder 12 to engage the upper portion of the gas cylinder 12 within the encapsulating device 10. The spring member 28 is movable to a second position wherein the lower portion of the spring member 28 substantially engages its respective leg 20 so that the gas sylinder 12 is removable from the encapsulating device 10. Alternately the spring member 28 may be attached to the ring 18 as shown in FIG. 5.

The second retainer means 26 comprises a retainer ring 30 disposed to surround and engage the gas cylinder 12 at or near the central portion thereof, the inside diameter of the retainer ring 30 being substantially equal to the outside diameter of the gas cylinder 12 but large enough that the gas cylinder 12 is easily movable in and out of the encapsulating device 10. As best shown in FIG. 4, the retainer ring 30 includes a recess 32 therein to at least partially engage each respective leg 20 between the wall of the gas cylinder 12 and the retainer ring 30. The second retainer means 24 further includes a holding means 34 for fixedly engaging the gas cylinder 12 for retention thereof in the encapsulating device 10. The holding means 34 comprises at least one threaded aperture 36 in the retainer ring 30 and a screw or threaded element 38 to engage each threaded aperture 36 and to fixedly engage the wall of the gas cylinder 12 wherein tightening of the screw 38 securely against the wall of the gas cylinder 12 will retain the gas cylinder 12 securely in place.

Each of the legs 20 engage the walls of the gas cylinder 12 between the upper portion of the retainer ring 30 and the lower portion of the gas cylinder 12. The legs 20 flare out between the upper portion of the retainer ring 30 and the protective ring 18 to connect with the protective ring 18.

The encapsulating device 10 further includes an attachment means 40 fixedly attached to the retainer ring 30 for the removable attachment of the encapsulating device 10 with gas cylinder 12 to the wall of a building or other structure for storage thereof and for quick removal for emergency use. The attachment means 40 comprises a slide member 42 which slides into an engages a groove in a corresponding member (into shown) on the wall or other structure.

The enclosure bag 48 is a bag made of canvas or other suitable durable material which is disposed around the outside of the cage assembly 16 and substantially encloses the gas cylinder 12. The enclosure bag 48 comprises at least one pair of flaps 44 for attachment of the enclosure bag 48 to the protective ring 18 and an opening means or zipper 59 which permits removal of the cage assembly 16 from the bag 48. Aperture 49 is provided to at least partially engage the screw 36 so that the screw 36 can be operated from outside of the enclosure bag 48. As shown in FIG. 2, an aperture 50 is provided to at least partially engage the slide member 42. At least one transparent pouch 52 is provided for the storage of hoses and other equipment therein so that the encapsulating device 10 is entirely self-contained. As envisioned, the pouch 52 may comprise several portions 53, 55 and 57 for storage of various elements. The opening means 46 comprises a zipper 59 disposed substantially the entire length of the enclosure bag 48. The hose is also storable between the enclosure bag 48 and the gas cylinder 12 and ring assembly 16 by the placement therein and the closing of the zipper 59. The hose may also be fed into the pouch 52 through an aperture (not shown) from the inside of the enclosure bag 48 so that it is not necessary that hose be exposed outside of the enclosure bag. Resusitating devices may be attached to the ends of the hoses and kept within the pouch so that, in emergencies, it is only necessary to reach into the pouch and remove the resusitating device and manipulate the valves on the valve and gauge assembly 14.

In an alternative embodiment of the protector ring 18, as shown in FIG. 5, the protective ring 18 has an annular portion 54 along three sides as previously described, and a flat portion 56 along the side on which the attachment means 40 is disposed. The flat portion 56 is disposed substantially the same distance from the central axis of the gas cylinder 12 as the attachment means 40 is disposed so that when stored on a wall by use of the attachment means 40, the cage assembly 16 will be disposed flat against the wall. Additionally, the protective ring 18 may be in shapes other than described as the circumstances may require.

In operation, the protective ring 18 acts as a convenient handle and the gas cylinder 12 is easily placed between a patient's legs while on a stretcher without the necessity of removal from the encapsulating device 10, the flared portion with the protective ring 18 being disposed away from the patient's head and the valves, gauges, and hoses being easily accessable. Because of the light weight of the encapsulating device 10, there is little temptation to remove the gas cylinder 12 therefrom.

In case of accidental dropping of the gas cylinder 12, the valve and gauge assembly 14 is protected from damage by the protective ring 18.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An encapsulating device for a gas cylinder having a valve and gauge assembly thereon for use with emergency medical equipment, said encapsulating device comprises an open cage assembly to enclose and protect the gas cylinder and valve and guage assembly, said open cage assembly comprises a protective ring disposed adjacent the valve and gauge assembly and a base to support the gas cylinder held in fixed spaced relation relative to each other by a plurality of legs extending therebetween to permit operation of the gas cylinder while within said encapsulating device, a first retainer means comprising an elongated flexible spring member movable between a first and second position attached to the upper portion of one of said legs wherein the lower portion of said spring member is disposed to engage the upper portion of the gas cylinder when in said first position to secure the gas cylinder device in said encapsulating device and to disengage the upper portion of the gas cylinder when in said second position to permit removal of the gas cylinder from said encapsulating device, a second retainer means to retain the gas cylinder within said open cage assembly comprising a retainer ring disposed to surround the gas cylinder at the mid portion thereof and a holding means to fixedly engage the gas cylinder for retention thereof in said encapsulating device, said protective ring being at least twice the diameter of said base such that said legs extending therebetween follow the natural anatomical contour of the patient's legs when in use, said encapsulating device further comprising an attachment means fixedly attached to said retainer ring for the removable attachment of said encapsulating device to the wall of a structure for storage.

2. The encapsulating device of claim 1 wherein said holding means comprises at least one threaded aperture in said retainer ring and a screw to at least partially engage said threaded aperture and to at least partially engage the wall of the gas cylinder wherein tightening of said screw securely against the wall of the gas cylinder will retain the gas cylinder securely in said encapsulating device.

3. The encapsulating device of claim 1 further comprising an enclosure bag disposed around the outside of said cage assembly to substantially enclose the gas cylinder.

4. The encapsulating device of claim 3 wherein said enclosure bag comprises at least one pouch for storage of hoses and equipment, an opening means for removal of said enclosure bag, and at least one pair of flaps for attachment of said enclosure bag to said protective ring for easy accessibility to the valve and gauge assembly.

5. The encapsulating device of claim 1 wherein said protective ring includes an annular portion and a flat portion, said flat portion being disposed on the same side of said cage assembly as said attachment means such that when said attachment means is used to store said gas cylinder on a wall, said cage assembly will be disposed flat against the wall.

6. The encapsulating device of claim 1 wherein said base comprises a cup like element attached to the lower portion of said pair of legs to surround the lower portion of the gas cylinder.

* * * * *